(12) United States Patent
Wurziger et al.

(10) Patent No.: US 6,977,304 B2
(45) Date of Patent: Dec. 20, 2005

(54) METHOD FOR PRODUCING INDOLES

(75) Inventors: Hanns Wurziger, Darmstadt (DE);
Guido Pieper, Mannheim (DE);
Norbert Schwesinger, Ilmenau (DE)

(73) Assignee: MERCK Patent GmbH, Darmstadt (DE)

( * ) Notice: Subject to any disclaimer, the term of this patent is extended or adjusted under 35 U.S.C. 154(b) by 117 days.

(21) Appl. No.: 10/296,465

(22) PCT Filed: Mar. 29, 2001

(86) PCT No.: PCT/EP01/03573

§ 371 (c)(1),
(2), (4) Date: May 28, 2003

(87) PCT Pub. No.: WO01/92225

PCT Pub. Date: Dec. 6, 2001

(65) Prior Publication Data

US 2003/0181733 A1    Sep. 25, 2003

(30) Foreign Application Priority Data

May 29, 2000 (DE) ............... 100 26 646

(51) Int. Cl.$^7$ .......................................... C07D 209/56
(52) U.S. Cl. ...................................................... 548/427
(58) Field of Search ........................................ 548/427

(56) References Cited

U.S. PATENT DOCUMENTS 4,273,711 A * 6/1981 Lauer et al. ................ 548/440

* cited by examiner

*Primary Examiner*—Taofiq Solola
*Assistant Examiner*—Robert Shiao
(74) *Attorney, Agent, or Firm*—Millen White Zelano & Branigan, P.C.

(57) ABSTRACT

The present invention relates to a process for the preparation of indoles.

25 Claims, No Drawings

METHOD FOR PRODUCING INDOLES

The present invention relates to a process for the preparation of indoles.

The preparation of indoles is of great importance to the chemical industry, which is also reflected in numerous publications on this subject.

However, the preparation of indoles on an industrial scale is accompanied by safety problems and risks. Firstly, use is frequently made of relatively large amounts of highly toxic chemical substances, which in themselves already represent a considerable risk to people and the environment, and secondly reactions for the preparation of indoles are frequently very highly exothermic, and consequently there is an increased risk of explosion when these reactions are carried out on an industrial scale. Obtaining official approval in accordance with emissions protection legislation for the operation of plants for the preparation of indoles on an industrial scale is therefore associated with considerable effort.

The object of the present invention is therefore to provide a process for the preparation of indoles which avoids the above-mentioned disadvantages. It should be possible to carry out this process, in particular, in a simple, reproducible manner with increased safety for people and the environment and with good yields, and it should be very readily possible to control the reaction conditions.

This object is achieved, surprisingly, by the process according to the invention for the preparation of indoles, in which at least one arylhydrazone in liquid or dissolved form is mixed with at least one catalyst in liquid or dissolved form in at least one, optionally heatable microreactor and reacted for a residence time, and the indole compound obtained in this way is, if desired, isolated from the reaction mixture.

Advantageous embodiments of the process according to the invention are described in the sub-claims.

A further preferred embodiment of the process according to the invention is characterised in that at least one arylhydrazone in liquid or dissolved form is heated and mixed in at least one heatable microreactor and reacted for a residence time, and the resultant indole compound is, if desired, isolated from the reaction mixture.

In accordance with the invention, individual arylhydrazones or mixtures of at least two arylhydrazones can be reacted by the claimed process. Preferably, in each case only one arylhydrazone is reacted by the process according to the invention.

For the purposes of the invention, a microreactor is a reactor having a volume of $\leq 1000$ $\mu$l in which the liquid(s) and/or solution(s) are intimately mixed at least once. The volume of the microreactor is preferably $\leq 100$ $\mu$l, particularly preferably $\leq 50$ $\mu$l.

The microreactor is preferably made from thin silicon structures connected to one another.

The microreactor is preferably a miniaturized flow reactor, particularly preferably a static micromixer. The microreactor is very particularly preferably a static micromixer as described in the patent application having the international publication number WO 96/30113, which is incorporated herein by way of reference and is regarded as part of the disclosure. A microreactor of this type has small channels in which liquids and/or chemical compounds in the form of solutions are mixed with one another by means of the kinetic energy of the flowing liquids and/or solutions.

The channels of the microreactor preferably have a diameter of from 10 to 1000 $\mu$m, particularly preferably from 20 to 800 $\mu$m and very particularly preferably from 30 to 400 $\mu$m.

The liquid(s) and/or solution(s) is (are) preferably pumped into the microreactor in such a way that they flow through the latter at a flow rate of from 0.01 $\mu$l/min to 100 ml/min, particularly preferably from 1 $\mu$l/min to 1 ml/min.

According to the invention, the microreactor is preferably connected via an outlet to at least one residence zone, preferably a capillary, particularly preferably a heatable capillary. The liquids and/or solutions are fed into this residence zone or capillary, after mixing in the microreactor, in order to extend their residence time.

For the purposes of the invention, the residence time is the time between mixing of the starting materials and work-up of the resultant reaction solution for analysis or isolation of the desired product(s).

The residence time necessary in the process according to the invention depends on various parameters, such as, for example, the temperature or reactivity of the starting materials. It is possible for the person skilled in the art to match the residence time to these parameters and thus to achieve an optimum course of the reaction.

The residence time of the reaction solution in the system used comprising at least one microreactor and, if desired, a residence zone can be adjusted through the choice of the flow rate of the liquid(s) and/or solution(s) employed.

The reaction mixture is likewise preferably passed through two or more microreactors connected in series. This achieves, even at an increased flow rate, an extension of the residence time, and the components employed are reacted in such a way that an optimum product yield of the desired indole/indoles is achieved.

In a further preferred embodiment, the reaction mixture is passed through two or more microreactors arranged in parallel in order to increase the throughput.

In another preferred embodiment of the process according to the invention, the number and arrangement of the channels in one or more microreactor(s) are varied in such a way that the residence time is extended, likewise resulting in an optimum yield of the desired indole(s) at the same time as an increased flow rate.

The residence time of the reaction solution in the microreactor, where appropriate in the microreactor and the residence zone, is preferably $\leq 15$ hours, preferably $\leq 3$ hours, particularly preferably $\leq 1$ hour.

The process according to the invention can be carried out in a very broad temperature range, which is essentially restricted by the heat resistance of the materials employed for the construction of the microreactor, any residence zone and further constituents, such as, for example, connections and seals, and by the physical properties of the solutions and/or liquids employed.

If the process according to the invention is carried out in the presence of a catalyst, it is preferably carried out at a temperature in the range from $-100$ to $+250°$ C., particularly preferably in the range from $-78$ to $+150°$ C. and very particularly preferably in the range from 0 to $+40°$ C.

If the process according to the invention is carried out without a catalyst, it is preferably carried out at a temperature in the range from 80 to 200° C., particularly preferably in the range from 90 to 150° C. and very particularly preferably in the range from 100 to 120° C.

The process according to the invention can be carried out either continuously or batchwise. It is preferably carried out continuously.

For carrying out the process according to the invention for the preparation of indoles, it is necessary for the reaction to be carried out as far as possible in the homogeneous liquid phase containing no or only very small solid particles, since otherwise the channels present in the microreactors become blocked.

The course of the reaction in the process according to the invention for the preparation df indoles can be followed using various analytical methods known to the person skilled in the art and if necessary regulated. The course of the reaction is preferably followed by chromatography, particularly preferably by high-pressure liquid chromatography, and if necessary regulated. In this case, control of the reaction is significantly improved compared with known processes.

After the reaction, the indole(s) is (are) isolated if desired. The indole(s) is (are) preferably isolated by extraction from the reaction mixture.

Arylhydrazones which can be employed in the process according to the invention are all arylhydrazones known to the person skilled in the art as substrates for the preparation of indoles.

In a preferred embodiment of the process according to the invention, use is made of at least one arylhydrazone of an organic ketone or of an organic aldehyde, particularly preferably an arylhydrazone of an aliphatic, aromatic or heteroaromatic ketone or an arylhydrazone of an aliphatic, aromatic or heteroaromatic aldehyde.

Suitable arylhydrazones of an aliphatic ketone or of an aliphatic aldehyde are all arylhydrazones of aliphatic ketones or aliphatic aldehydes which are known to the person skilled in the art and are suitable as substrates for the preparation of indoles. This also includes arylhydrazones of straight-chain, branched, cyclic, saturated and unsaturated ketones and/or arylhydrazones of straight-chain, branched, cyclic, saturated and unsaturated aldehydes.

Suitable arylhydrazones of an aromatic ketone or of an aromatic aldehyde are all arylhydrazones of aromatic ketones and/or aromatic aldehydes which are known to the person skilled in the art and are suitable as substrates for the preparation of indoles. For the purposes of the invention, this includes arylhydrazones of aromatic aldehydes and ketones which have a monocyclic and/or polycyclic homoaromatic basic structure or a corresponding moiety, for example in the form of substituents.

Suitable arylhydrazones of a heteroaromatic ketone or of a heteroaromatic aldehyde are all arylhydrazones of heteroaromatic ketones or heteroaromatic aldehydes which are known to the person skilled in the art and are suitable as substrates for the preparation of indoles and contain at least one heteroatom. For the purposes of the invention, arylhydrazones of heteroaromatic ketones or heteroaromatic aldehydes include arylhydrazones of heteroaromatic ketones or aldehydes which have at least one monocyclic and/or polycyclic heteroaromatic basic structure or a corresponding moiety, for example in the form of substituents. These heteroaromatic basic structures or moieties preferably have at least one oxygen, nitrogen and/or sulfur atom.

The arylhydrazones of aliphatic, aromatic or heteroaromatic ketones and aldehydes can be prepared by conventional methods known per se to the person skilled in the art. The arylhydrazones are preferably prepared by condensation of the corresponding arylhydrazines with the corresponding aliphatic, aromatic or heteroaromatic ketones or aldehydes.

In a further preferred embodiment of the process according to the invention, the arylhydrazone employed is a phenylhydrazine, particularly preferably a phenylhydrazone of an aliphatic, aromatic or heteroaromatic ketone or aldehyde.

in a further preferred embodiment of the process according to the invention, the arylhydrazone of the aliphatic, aromatic or heteroaromatic ketone and/or of the aliphatic, aromatic or heteroaromatic aldehyde is formed in situ in at least one micromixer, preferably from the corresponding arylhydrazine and the corresponding aliphatic, aromatic or heteroaromatic ketone and/or the corresponding aliphatic, aromatic or heteroaromatic aldehyde. For the purposes of the present invention, in-situ formation means that the arylhydrazone is formed immediately before conversion to the corresponding indole.

The arylhydrazone can likewise preferably be formed, preferably from the corresponding arylhydrazine and the corresponding aliphatic, aromatic or heteroaromatic ketone and/or the corresponding aliphatic, aromatic or heteroaromatic aldehyde, in at least one micromixer and isolated before conversion to the corresponding indole.

Catalysts which can be employed in the process according to the invention are all catalysts that are known to the person skilled in the art and are suitable for the preparation of indoles, or a mixture of at least two of these catalysts. Preferably, only one catalyst is employed in each case.

In a further preferred embodiment of the present invention, the catalyst employed is an inorganic acid, an organic acid, a Lewis acid or a mixture of at least two of these catalysts.

The inorganic acid employed can preferably be sulfuric acid, hydrochloric acid, perchloric acid, (poly)phosphoric acid, trifluoroacetic acid, nitric acid or a mixture of at least two of these inorganic acids.

The organic acid employed can preferably be chlorosulfonic acid, p-toluenesulfonic acid, methanesulfonic acid, trifluoromethanesulfonic acid or a mixture of at least two of these organic acids.

The Lewis acid employed can preferably be a boron/halogen compound, particularly preferably $BF_3$, a metal halide, particularly preferably $ZnCl_2$, $SnCl_4$, $AlCl_3$, $FeCl_3$, $TiCl_4$ or $MgCl_2$, very particularly preferably $ZnCl_2$, or a mixture of at least two of these Lewis acids.

In a further preferred embodiment, between 0.1 and 110 mol %, particularly preferably between 1 and 100 mol %, very particularly preferably between 10 and 50 mol %, of the catalyst(s) is employed, based on the amount of arylhydrazone(s) employed.

It is essential for the process according to the invention that the arylhydrazones employed and, if used, the catalysts are either themselves liquid or are in dissolved form. If the arylhydrazones employed or the catalysts are themselves liquid, they can, where appropriate, also themselves be employed as solvent for further components of the reaction. If they are not already themselves in liquid form, they must be dissolved in a suitable solvent before the process according to the invention is carried out. Preferred solvents are halogenated solvents, particularly preferably dichloromethane, chloroform, 1,2-dichloroethane or 1,1,2,2-tetrachloroethane, straight-chain, branched or cyclic paraffins, particularly preferably pentane, hexane, heptane, octane, cyclopentane, cyclohexane, cycloheptane or cyclooctane, or straight-chain, branched or cyclic ethers, particularly preferably diethyl ether, methyl tert-butyl ether, tetrahydrofuran or dioxane, aromatic solvents, particularly preferably toluene, xylenes, ligroin or phenyl ether, N-containing heterocyclic solvents, particularly preferably pyridine or N-methylpyrrolidone, or a mixture of at least two of these solvents.

In the process according to the invention, the risk to people and the environment due to released chemicals is considerably reduced and thus results in increased safety in the handling of hazardous materials. The preparation of indoles by the process according to the invention furthermore enables better control of the reaction conditions, such as, for example, reaction duration and reaction temperature, than is possible in the conventional processes. Furthermore, the risk of explosions in the case of very highly exothermic reactions for the preparation of indoles is significantly reduced in the process according to the invention. The temperature can be selected individually and kept constant in each volume unit of the system. The course of the reaction in the process according to the invention for the preparation of indoles can be regulated very quickly and precisely. The indoles can thus be obtained in very good and reproducible yields.

It is also particularly advantageous that the process according to the invention can be carried out continuously. This makes it faster and less expensive compared with conventional processes, and it is possible to prepare any desired amounts of the indoles without major measurement and regulation effort.

The invention is explained below with reference to an example. This example serves merely to explain the invention and does not restrict the general inventive idea.

EXAMPLE

Preparation of 1,2,3,4-Tetrahydrocarbazol-4-One From Phenylhydrazine and 1,3-Cyclohexanedione The preparation of 1,2,3,4-tetrahydrocarbazol-4-one from phenylhydrazine and 1,3-cyclohexanedione was carried out in a static micromixer (Technical University of llmenau, Faculty of Machine Construction, Dr.-lng. Norbert Schwesinger, PO Box 100565, D-98684, llmenau) having a physical size of 40 mm ×25 mm ×1 mm and having a total of 11 mixing stages with a volume of $0.125\,\mu l$ each. The total pressure loss was about 1000 Pa.

The static micromixer was connected via an outlet and an Omnifit medium-pressure HPLC connector (Omnifit, Great Britain) to a Teflon capillary having an internal diameter of 0.49 mm and a length of 1.0 m. The reaction was carried out at 100° C. To this end, the temperature of the static micromixer and the Teflon capillary were controlled in a thermostatted double-jacket vessel.

A 2 ml disposable syringe was filled with one part of a solution of 1.0 g (10 mmol) of phenylhydrazine in 40.5 ml of 50% sulfuric acid, and a further 2 ml disposable syringe was filled with one part of a solution of 1.1 g (10 mmol) of 1,3-cyclohexanedione in 40.5 ml of 50% sulfuric acid. The contents of the two syringes were subsequently transferred into the static micromixer using a metering pump (Harvard Apparatus Inc., Pump 22, South Natick, Mass., USA).

Before the reaction was carried out, the experimental arrangement was calibrated with respect to the dependence of the residence time on the pump flow rate. The residence time was set to 1; 2.5; 5; 10; 15; 20; 25; 30; and 60 minutes. The reactions were followed with the aid of a Merck Hitachi LaChrom HPLC instrument. The starting material to product ratio corresponding to the respective reaction conditions and residence times was determined by means of HPLC in the above-mentioned instrument.

What is claimed is:

1. A process for preparing indoles, comprising mixing at least one arylhydrazone in liquid or dissolved form with at least one catalyst in liquid or dissolved form, in at least one microreactor which is optionally heated, and reacting for a residence time sufficient to convert the arylhydrazone to an indole compound, and optionally isolating the indole compound.

2. A process according to claim 1, wherein the process is conducted at −100–+250° C.

3. A process according to claim 1, wherein the catalyst employed is an inorganic acid, an organic acid, a Lewis acid, or a mixture of at least two of these catalysts.

4. A process according to claim 3, wherein the inorganic acid is employed, and is a sulfuric acid, a hydrochloric acid, a perchloric acid, a (poly)phosphoric acid, a trifluoroacetic acid a nitric acid or a mixture of at least two of these inorganic acids.

5. A process according to claim 3, wherein the organic acid is employed, and is a chlorosulfonic acid, a p-toluenesulfonic acid, a methanesulfonic acid, a trifluoromethanesulfonic acid or a mixture of at least two of these organic acids.

6. A process according to claim 3, wherein the Lewis acid is employed, and is a boron/halogen compound, a metal halide, or a mixture thereof.

7. A process according to claim 1, wherein 0.1–110 mol %, of the catalyst(s) is employed, based on the amount of arylhydrazone(s) employed.

8. A process for preparing indoles, comprising heating and mixing at least one arylhydrazone in liquid or dissolved form, in at least one microreactor and reacting for a residence time sufficient to convert the arylhydrazones to an indoles, and optionally isolating the resultant indoles.

9. A process according to claim 8, wherein the process is conducted at 80–200° C.

10. A process according to claim 1, wherein the microreactor is a miniaturized flow reactor.

11. A process according to claim 1, wherein the microreactor is a static micromixer.

12. A process according to claim 1, wherein the microreactor is connected via an outlet to a capillary.

13. A process according to claim 1, wherein the volume of the microreactor is $\leq 100\,\mu l$.

14. A process according to claim 1, wherein the microreactor has channels having a diameter of 10–1000 $\mu m$.

15. A process according to claim 1, wherein the reaction mixture flows through the microreactor at a flow rate of 0.01 $\mu l$/min–100 ml/min.

16. A process according to claim 1, wherein the residence time of the compounds in the microreactor, is $\leq 15$ hours.

17. A process according to claim 1, further comprising analyzing the reaction products by chromatography.

18. A process according to claim 1, wherein the indole compound is isolated from the reaction mixture by extraction.

19. A process according to claim 1, wherein the arylhydrazone employed is prepared by reacting an arylhydrazine with an organic ketone.

20. A process according to claim 1, wherein the arylhydrazone employed is an arylhydrazone prepared by reacting an arylhydrazine with an organic aldehyde.

21. A process according to claim 1, wherein the arylhydrazone employed is a phenylhydrazone.

22. A process according to claim 1, wherein the aylhydrazone is formed in situ.

23. A process according to claim 1, wherein the arylhydrazone is formed in at least one micromixer and is isolated before conversion into the corresponding indole compound.

24. A process according to claim 12, wherein the residence time of the compound in the microreactor and the capillaries is $\leq 15$ hours.

25. A process according to claim 1, wherein the indole compound is 1,2,3,4-tetrahydrocarbazol-4-one.

* * * * *